United States Patent
Huang

(10) Patent No.: US 6,196,527 B1
(45) Date of Patent: Mar. 6, 2001

(54) HUMIDIFIER CAPABLE OF SENDING FORTH FRAGRANCE

(75) Inventor: Huang-Ming Huang, Tainan (TW)

(73) Assignee: Tyron Electric Ind. Co., Ltd., Tainan (TW)

( * ) Notice: Subject to any disclaimer, the term of this patent is extended or adjusted under 35 U.S.C. 154(b) by 0 days.

(21) Appl. No.: 09/305,365

(22) Filed: May 5, 1999

(51) Int. Cl.$^7$ ........................................ B01F 3/04
(52) U.S. Cl. ........................ 261/142; 261/DIG. 65; 261/DIG. 89
(58) Field of Search ................ 261/72.1, 74, 142, 261/DIG. 65, DIG. 88, DIG. 89; 96/222

(56) References Cited

U.S. PATENT DOCUMENTS

| | | | |
|---|---|---|---|
| 4,165,835 | * 8/1979 | Dearling | 261/DIG. 88 |
| 4,464,316 | * 8/1984 | Michaels | 261/DIG. 65 |
| 4,617,157 | * 10/1986 | Stein et al. | 261/DIG. 65 |
| 4,752,422 | * 6/1988 | Uchida et al. | 261/DIG. 65 |
| 4,906,417 | * 3/1990 | Gentry | 261/DIG. 65 |
| 5,247,604 | * 9/1993 | Chiu | 261/DIG. 65 |

* cited by examiner

*Primary Examiner*—C. Scott Bushey
(74) *Attorney, Agent, or Firm*—Rosenberg, Klein & Lee

(57) ABSTRACT

A humidifier capable of sending forth fragrance includes a housing, a water-detecting device, an electric heating member, a top covering and a perfume holding member. A water-containing hollow is provided within the housing. The detecting device and the heating member are arranged such that water held in the hollow can flow to both. The top covering is coupled to the housing, and has a steam-ejecting hole. The perfume holding member is coupled to, and covers a part of the ejecting hole. When the detecting device detects presence of water, the heating member will heat the water into steam, which is then ejected from the ejecting hole, and heats the perfume for it to be sent forth to the air.

2 Claims, 7 Drawing Sheets

HUMIDIFIER CAPABLE OF SENDING FORTH FRAGRANCE

BACKGROUND OF THE INVENTION

The present invention relates to a humidifier, particularly to one which can send forth fragrance.

Referring to FIG. 7, a heretofore known humidifier comprises a housing 10, a water tank 20, a steam passage member 30 and a top covering 40.

The housing 10 is provided with a water-containing hollow 101, a pushing projection 102, a water-detecting device 103 and an electric heating member 104. The pushing projection 102 is arranged on the center of the hollow 101. The hollow 101, the water-detecting device 103 and the electric heating member 104 are arranged such that water in the hollow 101 can flow to the detecting device 103 and the electric heating member 104.

The water tank 20 has a covering 201 screwed onto a bottom thereof. A valve 202 is fitted to the covering 201. The water tank 20 is positioned in the housing 10 with the valve 202 contacting the top end of the pushing projection 102. Thus, the valve 202 is opened to permit water inside the tank 20 to flow therethrough by the pushing projection 102.

The steam passage member 30 is positioned above the electric heating member inside the housing 10. The top covering 40 is coupled to the housing 10 with a steam outlet 401 arranged in open communication with the steam passage member 30.

In using the humidifier, the electic heating member 104 will heat the water thereon into steam when the water-detecting device 103 detects presence of water. The steam is then ejected to the outside through the steam passage member 30 and the steam outlet 401.

The humidifier can only humidify the surroundings without other functions i.e. the function of the humidifier is too limited to appeal to the customers.

SUMMARY

It is a main object of the present invention to provide a humidifier. It not only can humidify the air but send forth fragrance. The humidifier capable of sending forth fragrance of the present invention comprises:

a housing having a water containing hollow therein;

a water-detecting device housed in said housing;

an electrical heating member housed in said housing for heating water into steam when said detecting device detects presence of water;

a top covering coupled to said housing, said top covering having an ejecting hole for said steam to pass therethrough;

a perfume holding member coupled to and covering a part of said ejecting hole of said covering; thus, said steam is ejected through said ejecting hole to humidify the air and to heat the perfume holding member for the perfume held in the holding member to be sent forth to the air rapidly.

The ejecting hole has several radially arranged compartment walls, and two opposing curved locating plates therein. The locating plates are each connected to respective ones of the compartment walls, and each has a slot retaining a respective one of two protrusions on a bottom extension portion of said perfume holding member for said holding member to be removably coupled to said ejecting hole.

Herbs, which are fragrant or have soothing effect, can also be used in the perfume holding member in order for the humidifier to send forth the fragrance.

BRIEF DESCRIPTION OF THE DRAWINGS

The present invention will be better understood with reference to the accompanying drawings, wherein.

DETAILED DESCRIPTION OF THE PREFERRED EMBODIMENT

Figure 1:
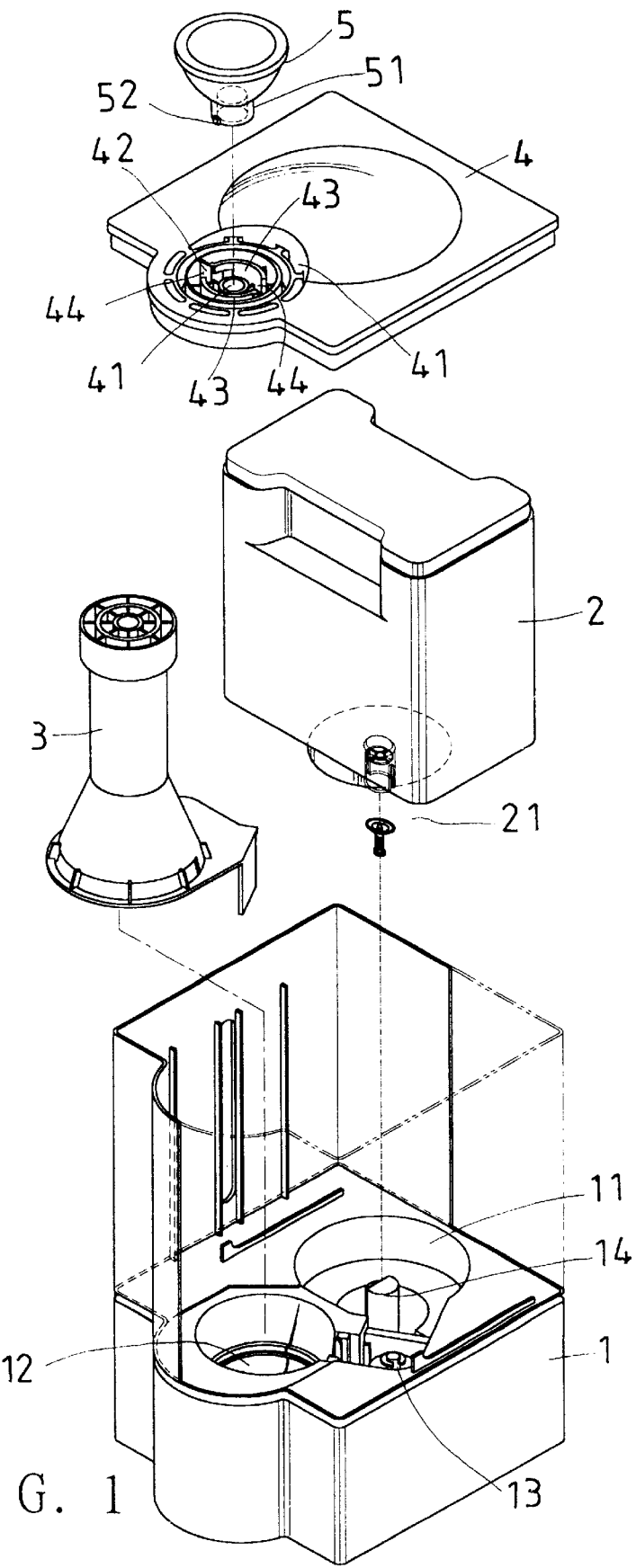
FIG. 1 is an exploded perspective view of a humidifier capable of sending forth fragrance according to the present invention.
Figure 2:
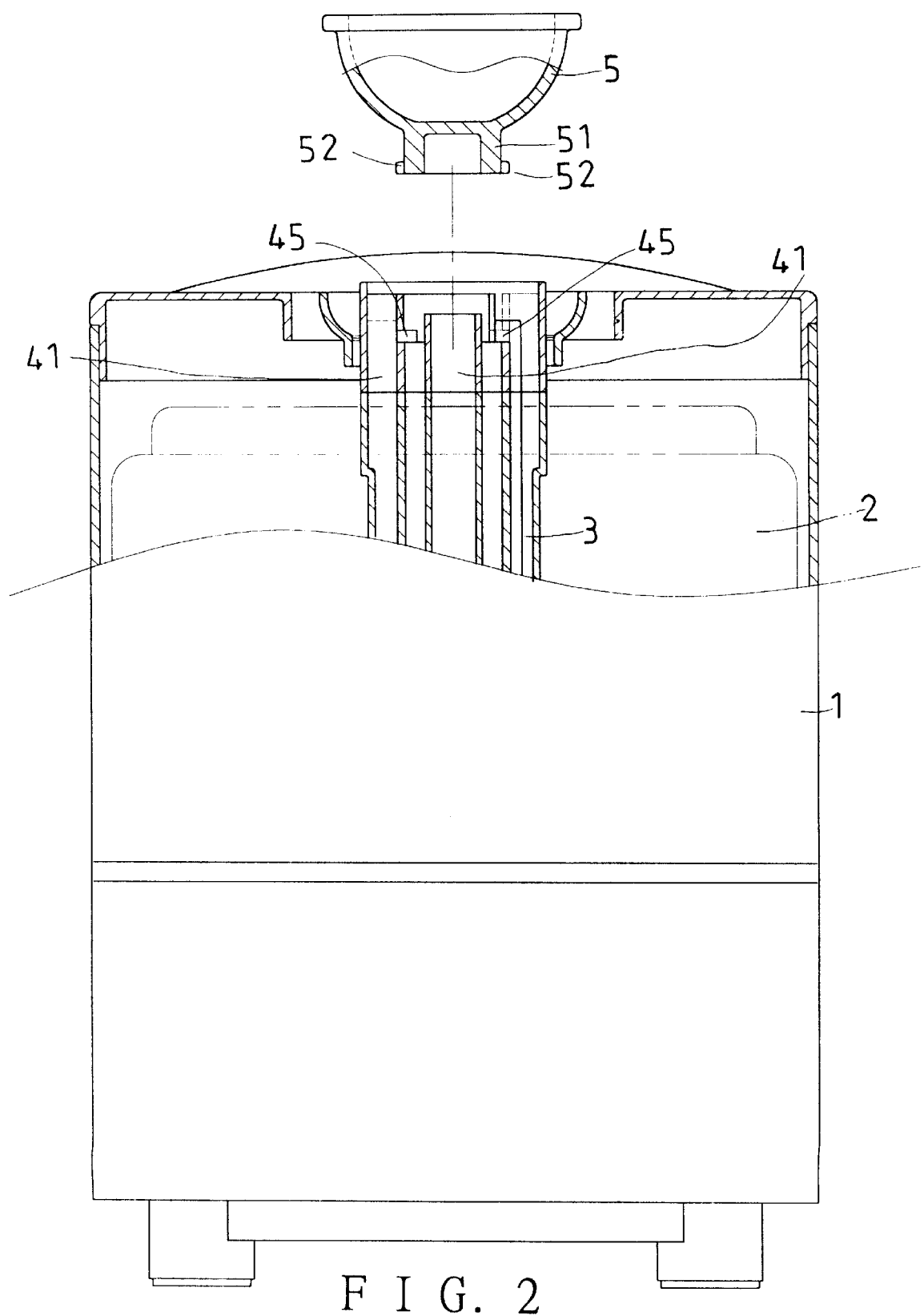
FIG. 2 is a fragmentary cross-sectional view of the humidifier capable of sending forth fragrance according to the present invention.
Figure 3:
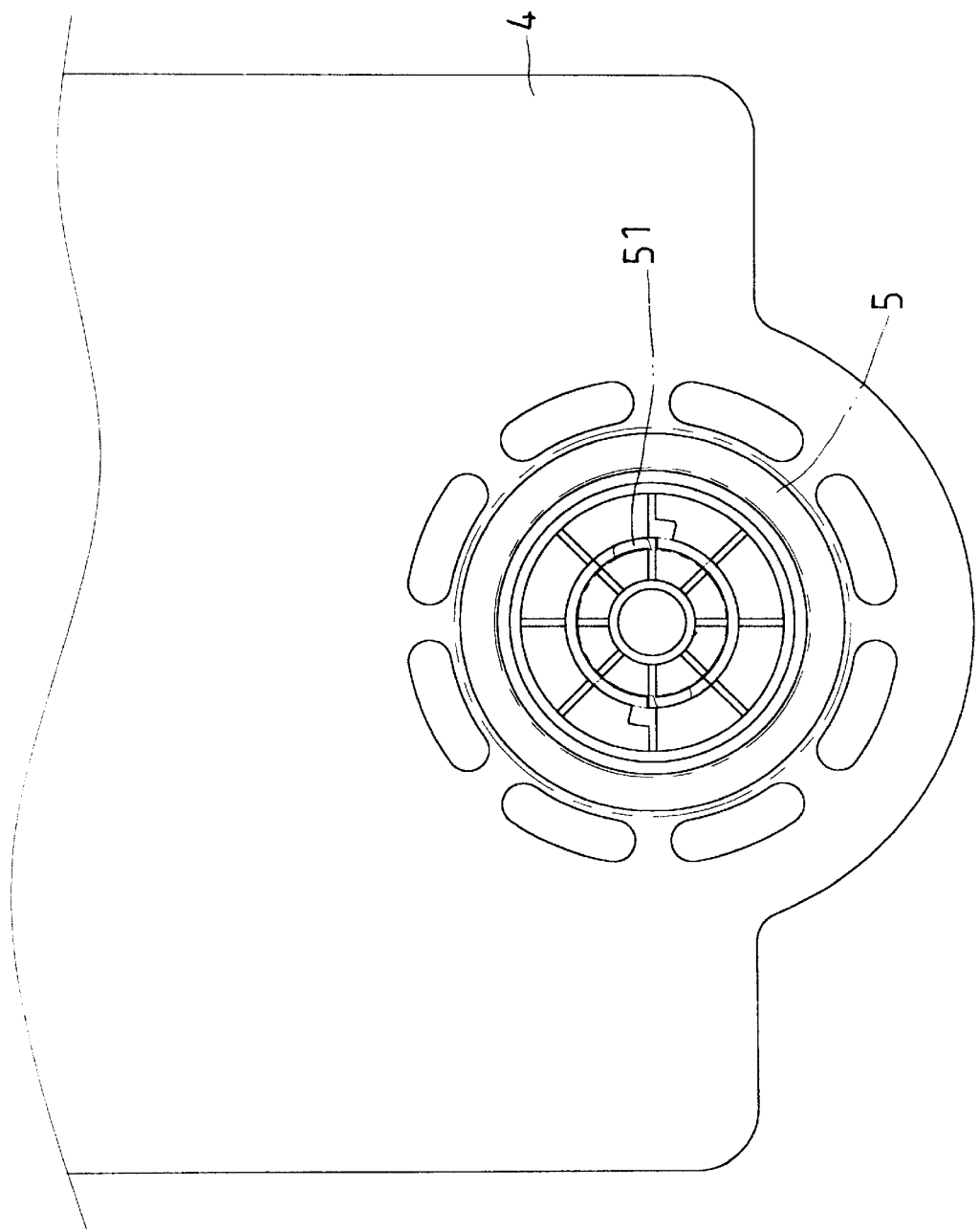
FIG. 3 is a top view of the top covering and the perfume holding member according to the present invention.
Figure 4:
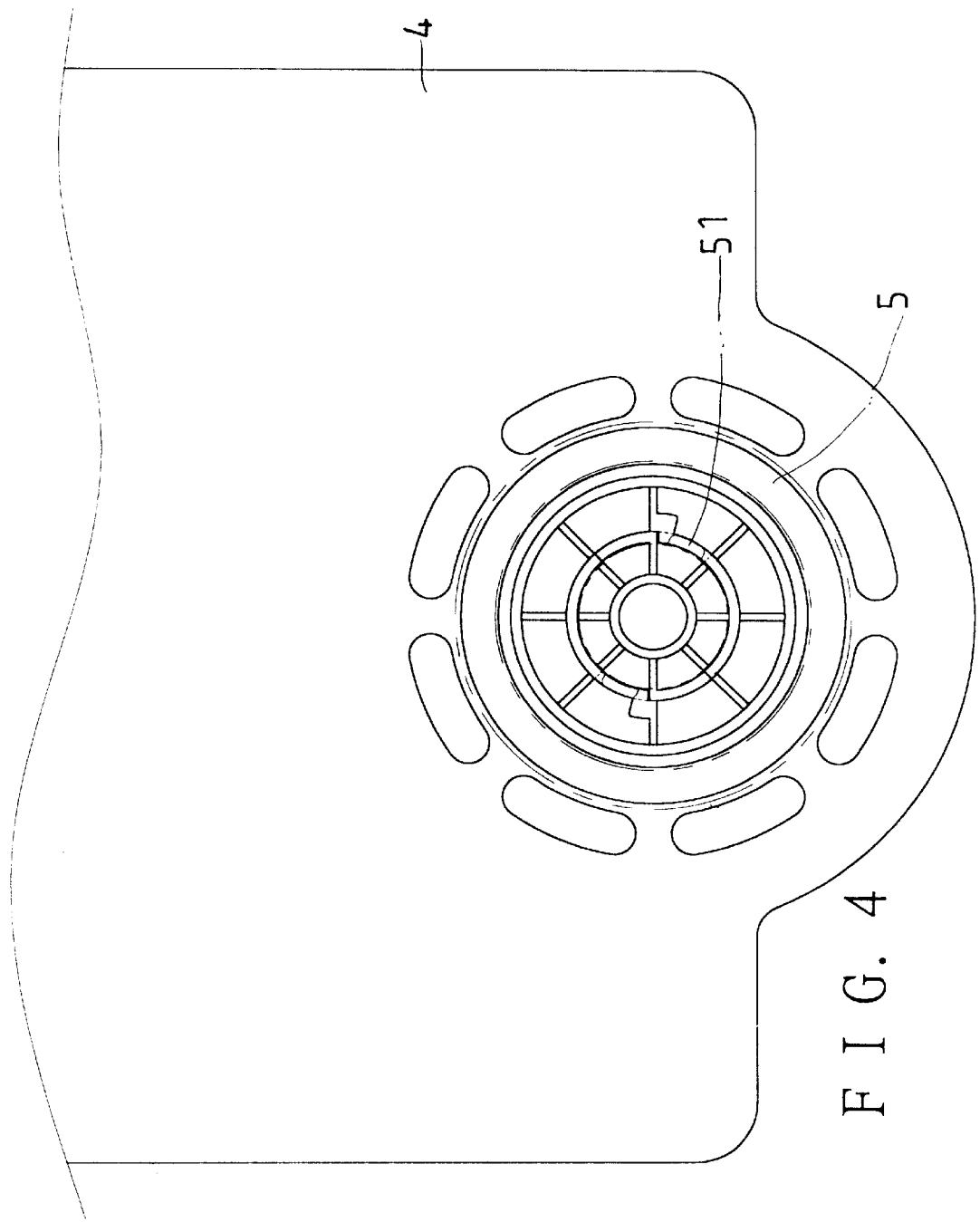
FIG. 4 is another top view of the top covering and the perfume holding member according to the present invention with both combined together.
Figure 5:
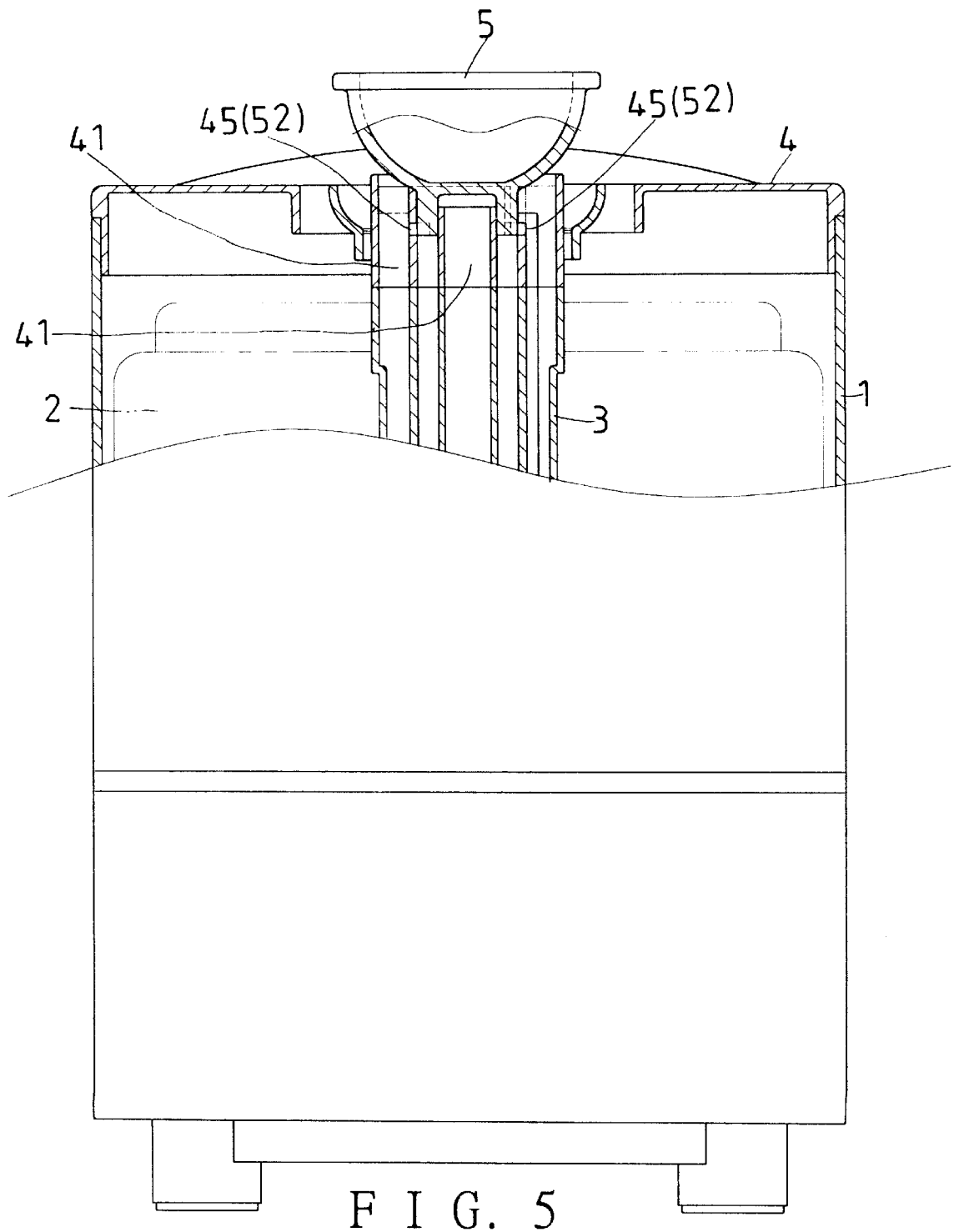
FIG. 5 is another fragmentary cross-sectional view of the humidifier in FIG. 1, with perfume holding member coupled to the top covering.
Figure 6:
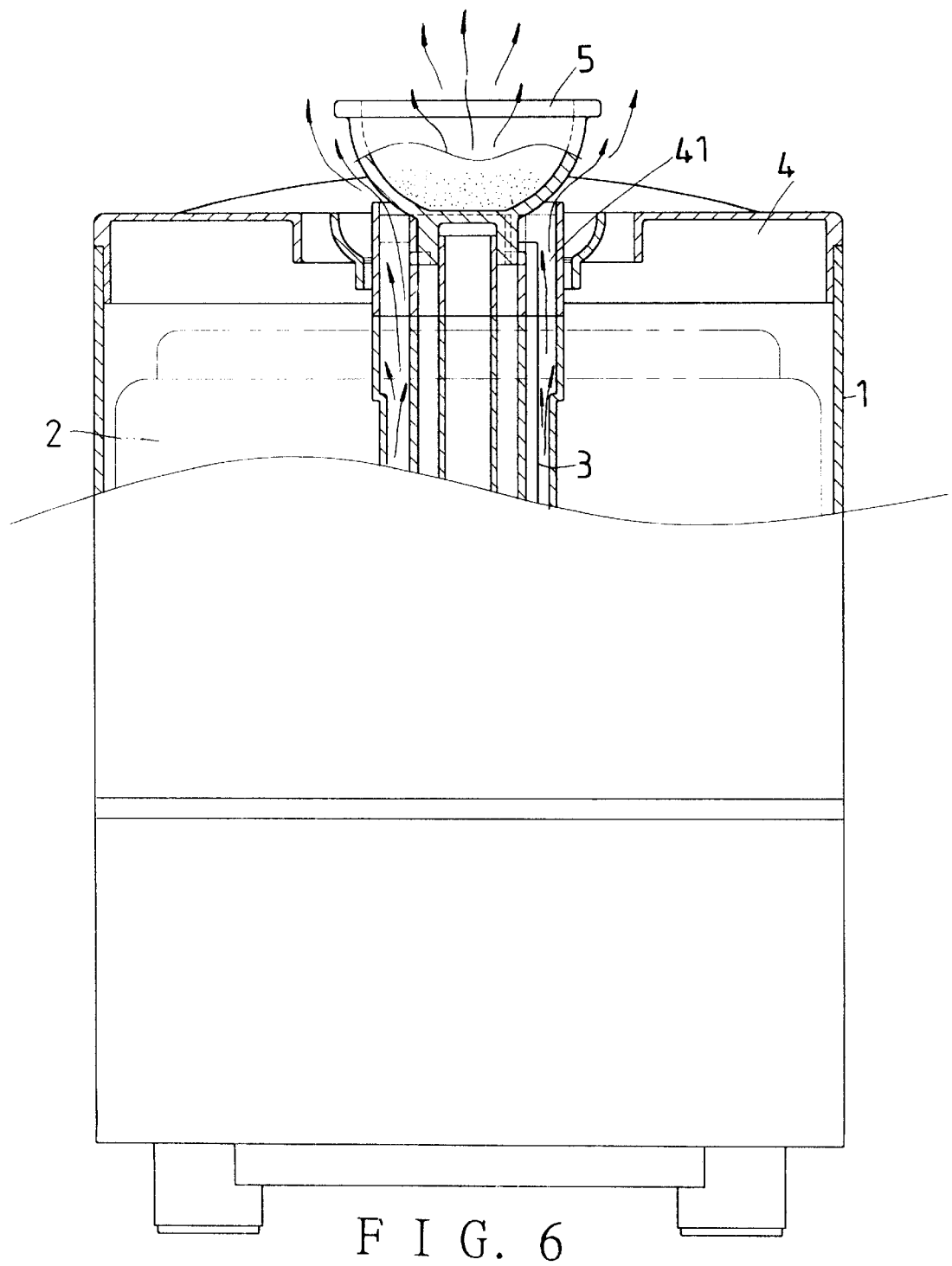
FIG. 6 is a view of the humidifier under use according to the present invention.
Figure 7:
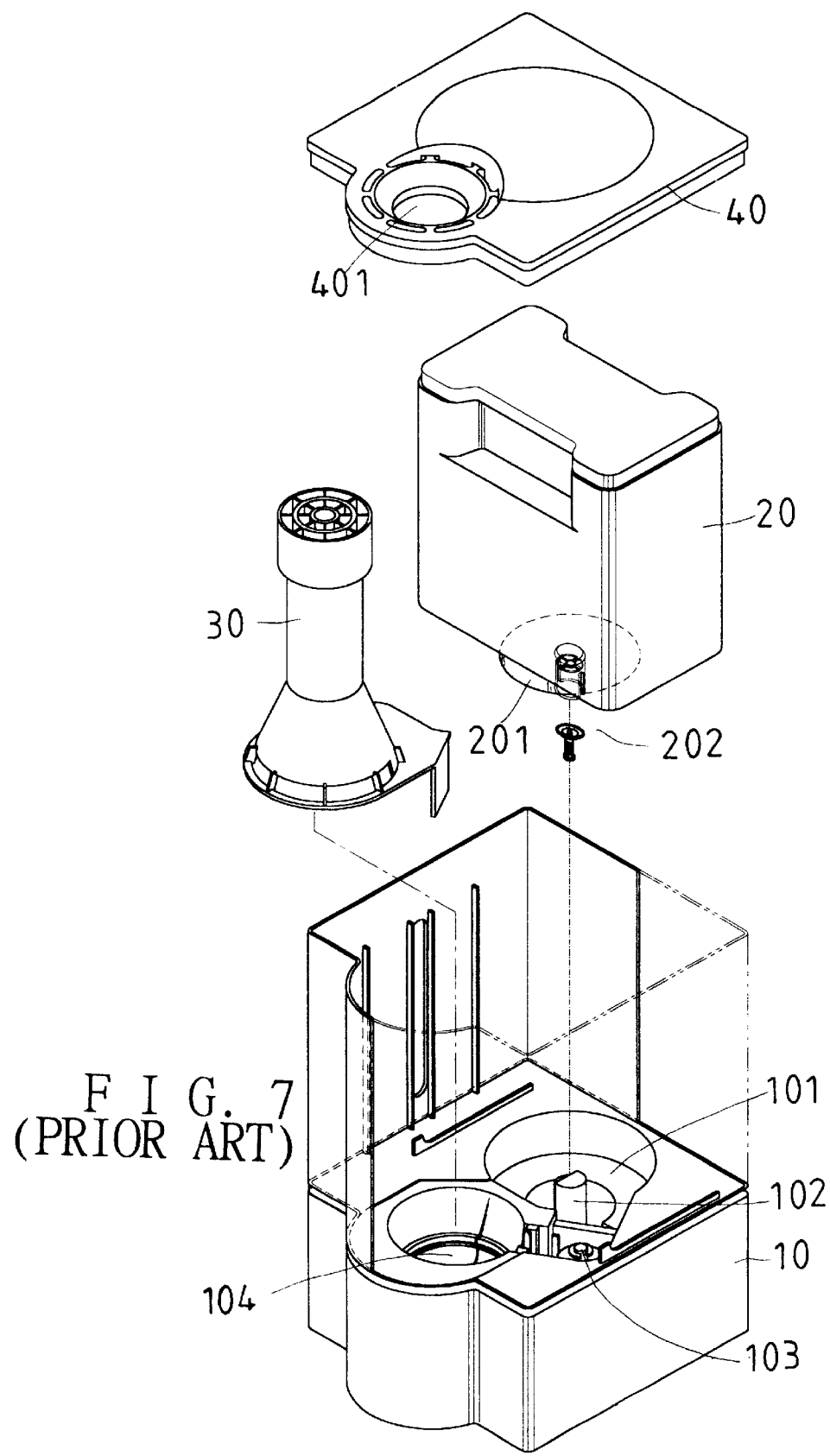
FIG. 7 is an exploded perspective view of a prior art humidifier.

Referring to FIGS. 1 and 2, a humidifier capable of sending forth fragrance of the present invention comprises a housing 1, a water tank 2, a steam passage member 3, a top covering 4 and a perfume holding member 5 as the main parts.

The housing 1 has a water-containing hollow 11, an electric heating member 12, a water-detecting device 13 and a pushing projection 14. The pushing projection 14 is located in the center of the hollow 11. The water-containing-hollow 11, the detecting device 13 and the heating-member 12 are arranged such that water inside the hollow 11 can flow to the detecting device 13 and the heating member 12.

The water tank 2 is positioned inside the housing 1 with a valve 21 contacting the top end of the pushing projection 14. Thus, when the water tank 2 is arranged in the proper position inside the housing 1, the valve 21 is opened by the projection 14 and allows water inside the tank 2 to flow therethrough.

The steam passage member 3 is positioned above the electric heating member 12 inside the housing 1.

The top covering 4 is coupled to the housing 1, and has an ejecting hole 41 in open communication with the steam passage member 3. The ejecting hole 41 has a plurality of radially arranged compartment walls 42. Two opposing curved locating plates 43 are each connected to respective ones of the compartment walls 42 with intermediate rooms 44 formed in between. A first slot 45 is formed on the lateral side of one 4 of the locating plates 43, and extended to the compartment wall 42 connected to the lateral side where the first slot 45 is formed. Similarly, a second slot 45 is formed on a lateral side of the other locating plate 43 in the opposite end, and extended to the compartment wall 42 connected to the lateral side where the second slot 45 is formed.

The perfume holding member 5 has an extension portion 51 and two protrusions 52 on the extension portion 51. The holding member 5 is coupled to the top covering 4 with the extension portion 51 received between the locating plates 43, the intermediate rooms 44 permitting the protrusions to be passed therethrough. The holding member 5 is turned for the protrusions 52 to be retained in a respective one of the slots 42 after the extension portion 51 is passed into between the locating plates 43.

In using the humidifier capable of sending forth fragrance, the heating member 12 heats the water thereon into steam when the detecting device 13 detects presence of water. The steam is then ejected through the steam passage member 3 to the ejecting hole 41; part of the steam will be ejected to the air; and, the other will get into contact with the holding member 5, and heat the perfume inside the holding member 5. Consequently, the perfume, after having been heated, will be sent out to the air more rapidly, mating the air fragrant.

From the above description, it can be understood that the humidifier not only can humidify the air but send forth fragrance. In addition, herbs can also be used in the perfume holding member to soothe the nerves of people.

What is claimed is:

1. A humidifier for generating fragrant vapor comprising:
   (a) a housing having a water storage chamber defined therein;
   (b) a detecting device disposed in said housing for detecting the presence of water in said water storage chamber of said housing;
   (c) an electric heating member disposed in said housing for converting at least a portion of the water in said housing to steam responsive to said detection by said detecting device of water presence;
   (d) a top covering coupled to said housing, said top covering defining an ejecting hole portion for releasing therethrough the steam generated by said electric heating member, said ejecting hole portion including a plurality of radially extended compartment wall segments and at least a pair of opposed arcuate locating plate segments coupled thereto, said arcuate locating plate segments each having a retaining slot formed therein; and,
   (e) a perfume holding member coupled to said top covering to extend over at least a portion of said ejecting hole portion, said perfume holding member including a bottom extension portion having a plurality of protrusions protruding therefrom, each said protrusion engaging one said retaining slot of said top covering;
   whereby a perfume material contained in said perfume holding member is vaporized responsive to the release of steam through said ejecting hole portion of said top covering.

2. A humidifier for generating fragrant vapor comprising:
   (a) a housing having a water storage chamber defined therein;
   (b) a detecting device disposed in said housing for detecting the presence of water in said water storage chamber of said housing;
   (c) an electric heating member disposed in said housing for converting at least a portion of the water in said housing to steam responsive to said detection by said detecting device of water presence;
   (d) a top covering coupled to said housing, said top covering defining an ejecting hole portion for releasing therethrough the steam generated by said electric heating member, said ejecting hole portion including a plurality of arcuate locating plate segments each having at least one retaining slot formed therein; and,
   (e) a perfume holding member detachably coupled to said top covering to extend over at least a portion of said ejecting hole portion, said perfume holding member including a bottom extension portion having a plurality of protrusions protruding therefrom, said protrusions each engaging in releasably locked manner one said retaining slot of said top covering;
   whereby a perfume material contained in said perfume holding member is vaporized responsive to the release of steam through said ejecting hole portion of said top covering.

\* \* \* \* \*